United States Patent [19]

Takahata

[11] Patent Number: 5,039,615

[45] Date of Patent: Aug. 13, 1991

[54] METHOD FOR CHEMICALLY ANALYZING A TEST PIECE

[75] Inventor: Ichiro Takahata, Kyoto, Japan

[73] Assignee: Kabushiki Kaisha Kyoto Daiichi Kagaku, Kyoto, Japan

[21] Appl. No.: 179,200

[22] Filed: Apr. 8, 1988

[30] Foreign Application Priority Data

Apr. 11, 1987 [JP] Japan .................................. 62-055044

[51] Int. Cl.$^5$ .............................................. C01N 21/00
[52] U.S. Cl. ........................................ 436/44; 436/47; 436/165; 436/171; 436/808; 422/63; 422/65; 422/66; 435/300; 435/301
[58] Field of Search ...................... 422/56, 3, 390, 100, 422/62, 249, 999, 63, 65, 104, 58, 66; 436/44, 46, 47, 164, 165, 807, 808, 171; 435/300, 301

[56] References Cited

U.S. PATENT DOCUMENTS 4,584,275  4/1986  Okano et al. .......................... 435/290

Primary Examiner—David L. Lacey
Assistant Examiner—David Redding
Attorney, Agent, or Firm—Darby & Darby

[57] ABSTRACT

An apparatus for chemically analyzing a sample on a test piece that includes a reagent layer, comprises a test piece table for positioning a test piece thereon, and an applying station wherein a sample may be applied to the reagent layer. The test table moves to a position below a row of holes with the reagents aligned to the holes and a sample is applied to each reagent layer from a nozzle, the samples passing through the respective holes. Covers are moved over the holes after the samples are applied and the test pieces are moved to a measuring station for measuring the reaction between the sample and reagent layer. Photometric techniques are used in evaluating the reaction. Opening and closing of the covers is controlled by motion of the sample dispensing nozzle as it moves from one opening to the next.

8 Claims, 4 Drawing Sheets

FIG. 3

METHOD FOR CHEMICALLY ANALYZING A TEST PIECE

BACKGROUND OF THE INVENTION

This invention relates to a biochemical analysis apparatus for chemically analyzing and measuring the characteristics of a body fluid, particularly blood, by using a test piece having a layer containing a reagent, and more particularly to the improvement of an apparatus for applying a sample to each reagent layer of a multi-item test piece or to each reagent layer of several single item test pieces set on a test piece table.

For biochemically analyzing blood (plasma, serum, whole blood) for the presence, quantity, and change of special components, a wet system using liquid reagents is available and also a dry system using solid phase reagents is available. In the latter system, a test piece is used wherein filter paper or a film is impregnated or coated with a reagent. Such a test piece is readily utilized in combination with a conventional apparatus including a reflectometer, and such test pieces have been generally used as a bedside test for an inpatient or as an instantaneous real time test for an outpatient.

Measurement technology has made substantial progress along with the progress in reagent and analysis instrumentation. By combination of the information in a single item measurement, such as glucose concentration and multi-components, a general diagnosis has been made of various diseases or organ disorders and in effect an evaluation of health has been synthesized to assist in treatment.

For example, by a set of tests of GOT, GPT, ALP, LAP, $\gamma$-GPT, and BUN in blood, a diagnosis of liver disorders is achieved. To assess the health of a patient in a first examination, blood sugar, creatinine, uric acid, BUN, cholesterol, TP, amylase, LDH, and GOT, are analyzed as a profile test. Additionally, there are several combinatorial analyses for the diagnosis of renal function or diabetes.

To conduct these combinatorial analyses in a short time, concurrent reactions and measurements of a number of items are necessary. Also, in a situation where a single item measurement is to be made on a multitude of samples, concurrent multimeasurement improves efficiency.

However, in the case of blood analysis, the applied sample quantity is extremely small, and by delaying evaluation after applying the sample to a test piece, a higher concentration tends to appear as the measured value because of water evaporation from the sample. Particularly, since the reaction proceeds at a relatively higher temperature (about 37° C.), evaporation is accelerated. Further, during a delay in making an evaluation, fluctuations in reaction temperature tend to occur.

To solve the above problems, for example, the table for holding a test piece has been made slidable into a photometric apparatus with a close fit. Also, a small closed space is provided. Immediately after applying the sample, the test piece is moved to the closed space. However, a moving mechanism for an individual test piece, that is, a single item test piece with a reagent layer, is extremely complex. Further, when an apparatus for evaluating a multi-item test piece with plural reagent layers using several of the same or different types, is used, which evaluates samples concurrently by plural measurement means, movement of an individual reagent layer test piece into the closed space is impossible.

SUMMARY OF THE INVENTION

The object of the invention is to solve the above problems and to assure accurate measurements with reproducible reactions by preventing evaporation of water from the samples applied to reagent layers and by keeping constant the reaction temperature of either a single item or a multi-item test piece in measurement of multi-items or multi-samples of a single item, such as a set or profile test. Further, the object of the invention is to speed up testing, diagnosis and treatment by concurrently conducting a combination of tests.

To attain these objects, a sample liquid applying station, is arranged on a test piece table close to a measuring station. The sample liquid applying station includes a plurality of applying holes that are arranged in a row with specified spacings therebetween. This row-arrangement of applying holes is generally parallel to the measurement station, and means are provided to maintain the temperature at the liquid applying station and at the measuring station. Each applying hole is fitted with a cover so that the applying hole may be closed after applying a sample to the reagent layer through the applying hole. This prevents water evaporation and temperature reduction. Further, opening or closing the cover is effected by a cover opening and closing rod moving in synchronism with a sample applying nozzle.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

Figure 3:
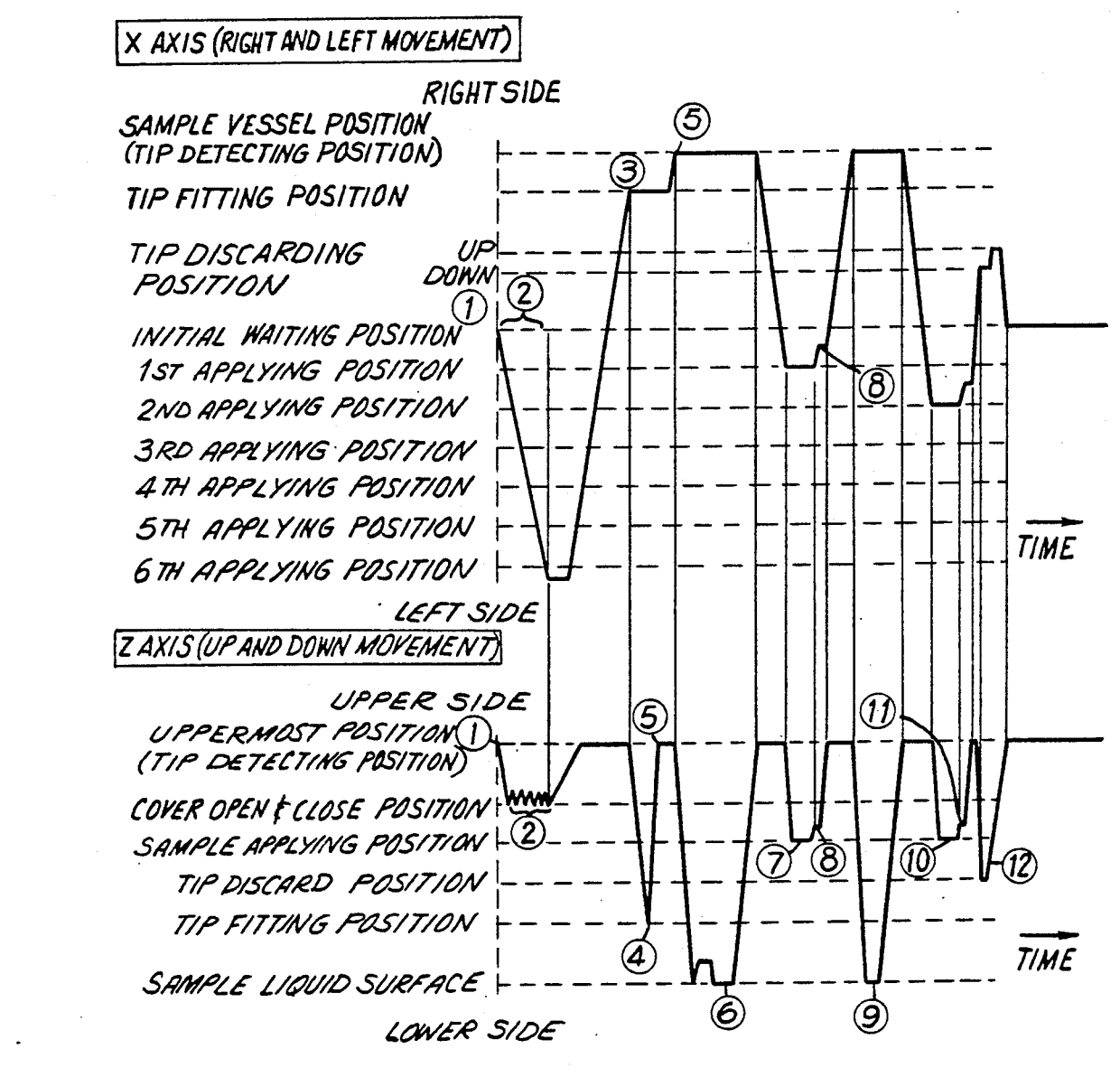

FIG. 3 is a graph showing movement of the nozzle assembly;

DESCRIPTION OF THE PREFERRED EMBODIMENTS

Figure 1:
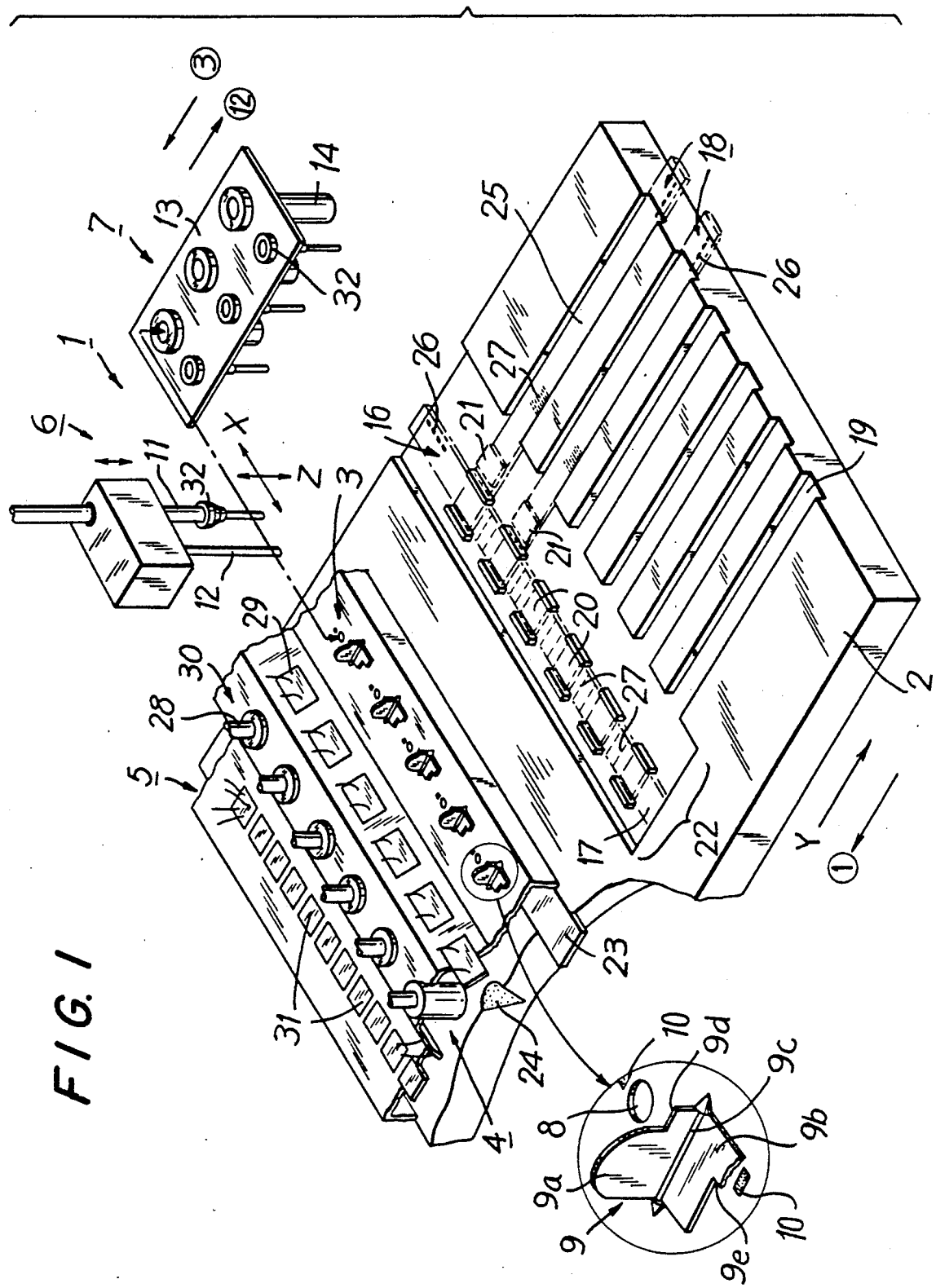
FIG. 1 is a top perspective view showing a portion of a biochemical analysis apparatus in accordance with the invention.

The test piece table of this specification refers to the table for setting test pieces thereon. The table has an arbitrary form, but in FIG. 1 is generally rectangular in shape. The table has space for receiving both a multi-item test piece and spaces each for receiving a single item test piece, though a test piece table having accommodation for only one or the other type of test pieces may also be used.

A station for a multi-item test piece positioned parallel to the length of a sample applying station is desirable. There may be one or several applying stations, but a single station is satisfactory. Several stations are generally available (FIG. 1) for positioning single item test pieces, and such test pieces are generally oriented at approximately 90° to the sample applying station. In a special construction, there may be accommodation for only one single item test piece.

A sample refers to a sample liquid, normally a body fluid, most frequently blood.

Applying refers to applying or sticking a sample of the sample liquid onto a reagent layer. Applying includes the techniques of dropping, contact sticking, and the like. Where a developing layer or other layer is present over a reagent layer, on a test piece, applying to the reagent layer means applying from above the other layer.

Though the order of applying a sample is arbitrary when there are more than one test items, it is preferable to apply a sample first to the reagent layer having the longer reaction time before measurement can start, so as to shorten the overall measuring time for the plurality of test items. Though application of the sample is performed only through applying holes below which a reagent layer exists, opening or closing of the covers over the holes may be performed for all applying holes.

A constant temperature room refers to a particular space having an inner portion maintained at a constant temperature. A space that is nearly closed and kept at a nearly constant temperature may also be usable, although it is not a constant temperature room in a strict sense. The volume of the constant temperature room is preferably small in order to reduce evaporation of water from the samples within the constant temperature room.

An applying part or station is the place for applying a sample to a reagent layer on a test piece in the analyzing apparatus of the invention.

An applying hole refers to a small opening through which a sample is applied from above to a reagent layer on a test piece when the test piece and reagent are positioned at the applying part or station. The form, arrangement, and disposition of the applying holes are arbitrary, but a sideways row of holes is convenient since this corresponds to the position of the reagent layers of a test piece. However, it is possible to change the position of the applying holes to correspond to changes in the arrangement of test pieces and for the arranged positions of the reagent layers on the test pieces. For example, circular or zig-zag arrangements may be used.

A cover refers to a component for covering an applying hole so as to suppress evaporation of water in a sample. The form of the cover is not specially limited, but L-shaped or slide-shutter type covers are convenient.

When all applying holes are closed by covers after applying the samples to the reagents, the test piece may be moved to the measuring stations at any time before measurements start.

A measurement start time refers to the elapsed time before measurement is practical after applying the sample. This time depends upon the calibration line used for conversion of measured values to concentrations of substances in the test liquid.

A measuring station refers to a place for measuring reflectivity after the sample/reagent reaction finishes, that is, after the measurement start time is over. The measuring station normally comprise a luminous portion and a light receiving portion. Besides measurement of reflectivity, measurement of fluorescence, obtained by radiation of the test item with an exciting light and measurement of voltage by contacting a voltage terminal, are suitable detection techniques.

FIG. 1 is an example of biochemical analyzing apparatus in accordance with the invention comprising a sample liquid applying apparatus 1. The apparatus 1 comprises a long, moveable test piece table 2, a sample liquid applying station 3 that is positioned to cover the upper part of the test piece table 2, a photometric station 4, a test piece evaluation station 5, a nozzle assembly 6, a sample holding assembly 7, an apparatus (not shown) for driving the moving elements as described hereinafter, and a microcomputer (not shown) for providing operating instructions and data storage.

The sample liquid applying apparatus 1 includes the sample liquid applying station 3 and the nozzle assembly 6.

Applying holes 8 are formed in the sample liquid applying part 3 at predetermined intervals, that is, corresponding to the position of the reagent layers of a test piece, described hereinafter. The applying holes 8 are formed through a plate of small width, and a cover 9 is fitted on each applying hole 8.

The cover 9, wherein a cover piece 9a and a moving piece 9b are joined into an L-shape and a supporting shaft 9c is fitted to the joint of the L-shape, turns on the supporting shaft 9c to close the applying holes with respective cover pieces 9a. Both the cover piece 9a and moving piece 9b are fitted with a respective notch 9d,9e. A magnet 10 is embedded in the surface in at least one position around each applying hole 8 to hold the associated cover and to prevent shaking or vibration of the cover 9.

The nozzle assembly 6 includes a nozzle 11 and a cover opening and closing rod 12, which in operation to apply samples are moved in the left-right direction (X axis) and in the up-down direction (Z axis). The nozzle 11 is fitted with a pipette tip 32, which sucks a sample 15 with the tip from the sample vessel 14 supported by a sample rack 13. The sample holding assembly 7 comprises the sample rack 13 and the driving assembly (not shown).

The test piece table 2 is moved in the direction of the Y axis (FIG. 1), that is, in forward and backward directions by a driving apparatus (not shown). On the test piece table 2, there is one lateral groove 17 that is transverse to the Y axis for receiving a multi-item test piece 16. There are also provided on the test piece table 2 a plurality of longitudinal grooves 19, that is, grooves parallel to the Y axis, for receiving therein single item test pieces 18. In FIG. 1, six such longitudinal grooves 19 are illustrated.

The lateral groove 17 is oriented parallel to the photometric station 4 and located near the center of the test piece table 2. The longitudinal grooves 19 are oriented at a right angle to the lateral groove 17 with each groove position corresponding to the position of a reagent layer when setting a multi-item test piece 16 in the lateral groove 17.

A heater (not shown) is mounted in the region of the lateral groove 17 and the fronts of the longitudinal grooves 19, that is, at the position of the reagent layers 20,21 (FIG. 1), to provide a constant temperature zone 22.

Forward of the lateral groove 17, a standard reflex piece 23 of white ceramic plate and several black damping cones 24 are located. These cones and plate are for calibration of reflectivity. The ceramic plate represents reflectivity of 100% and the cones represent reflectivity of 0%.

The test piece table 2 (FIG. 1) is a special construction useful for measurements on both a multi-item test piece 16 and single item test pieces 18.

In a multi-item test piece 16, plural reagent layers 20 retain reagents, which react with different substances in the test sample as necessary. For example, for the above-mentioned set test or profile test, respectively. The reagent layers are positioned in a known order with specified spacings. On a strip 25, a listing is provided near the base of the strip, of several measuring substances and/or names or notations 26 of a disease measurable by the test item, and a bar-code 27 (with notation of only one data bit at one position in relation to the reading direction) is provided as a means for identifying the test piece. Accordingly, accurate and rapid measurement is possible with no error in identification of test pieces and with labor saving in positioning many test pieces. In a set test, if another test item is necessary, it is supplemented by a single item test piece 18. The use of a multi-item test piece 16 with a plurality of identical reagent pads 20, is convenient for measurement of multi-samples of a special item.

Various changes are considered in the form and movement of the test piece table 2 in alternative embodiments in accordance with the invention. For example, there may be only the plurality of longitudinal grooves 19 or two or more lateral grooves 17, and a circular type test piece table 2 may also be used. Embodiments are constructed so that the positioning of test pieces, measurements, evaluations and item removal are operated in sequence by providing a plurality of lateral grooves 17 and different combinations of plural longitudinal grooves 19, these combinations being selected depending on the required testing capacity.

In the photometric station 4, measurement devices 30, and a combination of luminous part 28 and light receiving parts 29 are arranged in rows with specified spacings between them. The luminous elements 28 radiate a light (multi-wavelength) from a light source (not shown) onto each pad. For example, the light may be radiated from the end of a light fiber (light-guide) that is located over the position of the reagent layer. The light receiving part 29, composed of a light detector, receives light reflected from the surface of the reagent layer. As measurement devices 30, an integrating sphere and other such devices also may be used.

The test piece evaluation station 5 reads the bar-code 27 of each test piece. Therein a plurality of measurement devices 31, including a photo-interrupter, a combination of a luminous diode and a photo-transistor, are located in a row. The number of measurement devices 31 is greater than the number of measurement devices 30 of the photometric station 4 because of the difference of the position of the bar-codes 27 between the multi-item test pieces 16 and the single item test pieces 18.

In FIG. 1, by shifting the position of each longitudinal groove 19, the number of applying holes 8 at the sample liquid applying station 3 and of the measurement devices 30 at the photometric station 4 can be made equal. As a means for identifying each test piece 16,18, in place of a bar-code, a color notation, an eye hole, or a notch may be used, and a corresponding detecting device is used. Further, each reagent layer may be observed by transmitted light or fluorescence in place of reflected light.

A procedure for analyzing a blood sample (1 sample, 2 items) by the apparatus in accordance with the invention will be described hereinafter in accordance with the figures. The numerals enclosed in circles in each drawing indicate the sequence of operations in using the subject apparatus.

① First, the sample vessel 14, pipette tip 32, and a single item test piece 18 (two are shown in FIG. 1) are set to their specified positions respectively, and a start switch (not shown) is pushed.

The test piece table 2 moves in the Y direction so that the bar-code 27 on each test piece 18 is read by an aligned measuring device 31 at the test piece evaluation station 5. The measuring type (end-point method, rate method, etc.) of each test piece 18 and the time required until a measurement may start after reaction is initiated, are determined based on data stored in advance by a microcomputer (not shown). At the same time, the surface of each reagent layer is observed, and a wet layer, that is, somehow contaminated by a liquid other than the sample, may be eliminated as a measurement. During this time, the nozzle assembly 6 is in the ready or standby position.

Figure 4A:
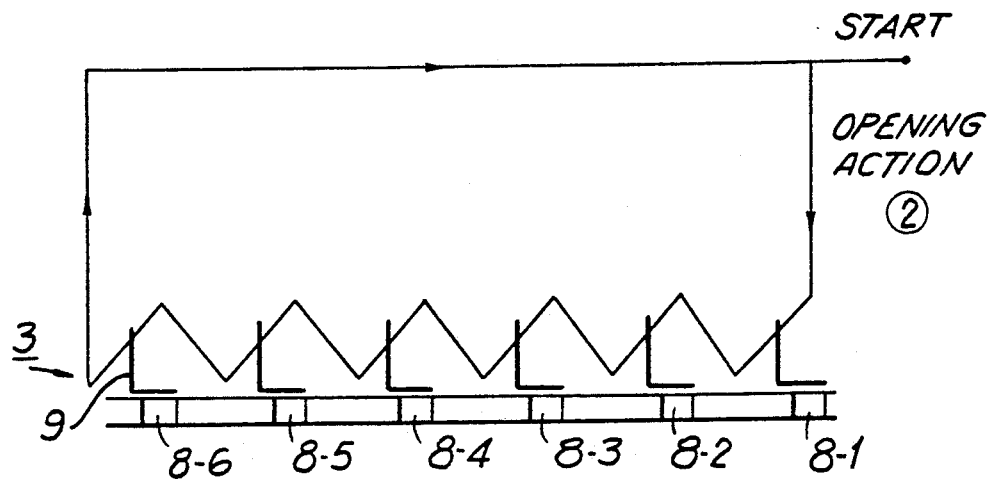
FIG. 4(a) illustrates the opening action of covers due to motion of the nozzle assembly.

② Next, the nozzle assembly 6 operates in a cover opening action. The opening action is effected, as illustrated in FIG. 4a by pushing down the moving piece 9b of the cover 9 by the opening-closing rod 12. This is accomplished by moving the nozzle part 6 up and down in a saw-like manner as the nozzle part 6 moves over the row of holes. Cover opening is effected from the first applying hole 8-1 to the sixth applying hole 8-6 in sequence. When only a single test piece 18 is being evaluated, this opening action may be effected only for the single applying hole 8 set over the test piece 18.

③ After opening all of the covers 9, the nozzle 11 moves to the position wherein the tip 32 is fitted to the nozzle 11. At the same time, the sample rack 13 is moved to a sampling position to prepare for sampling of the sample 15 in the vessel 14.

④ In a continuous motion, the nozzle assembly 6 moves down and the pipette tip 32 is fitted to the nozzle 11.

⑤ After fitting the tip 32, the nozzle 11 rises and moves to the left (FIG. 1) so that it comes over the sample vessel 14. Here, the pipette tip 32 is checked for a proper fitted position on the nozzle 11 by an optical tip detector 33.

⑥ When the fit is correct, the nozzle assembly 6 moves down and sucks the sample 15 into the pipette tip 32 after detecting a sample liquid level by the nozzle 11.

⑦ After sucking the sample 15 into the pipette tip 32, the nozzle assembly 6 rises, moves to the left and comes to a position over the first applying hole 8-1. The nozzle assembly 6 then descends continuously and applies a sample 15 through the hole 8 to the reagent layer 21 just below. At this time, the end of the cover opening-closing rod 12 is drawn back slightly by being pushed by the upper surface of the sample liquid applying station 3.

⑧ After applying the sample, the nozzle assembly 6 rises slightly and moves to the right and closes the cover by pushing the cover piece 9a with the cover opening/closing rod 12 (closing action).

Figure 4B:
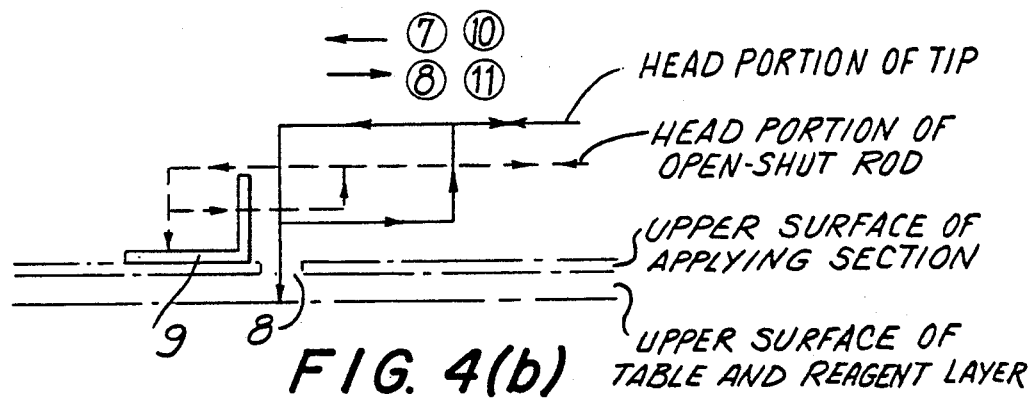
FIG. 4(b) is a graph showing the cover closing action.

Action of the nozzle assembly 6 in steps 7 and 8 is shown in FIG. 4b. The solid line arrow shows the action of the end of the tip 32, and the dotted line arrow shows the action of the end of the cover opening-closing rod 12.

When the cover 9 is an iron plate, and a weak magnet is located near the applying hole 8, shaking of the cover 9 is prevented and the opened and closed states of the cover pieces 9a are maintained stably, though some power is necessary in opening or closing the cover 9.

⑨ In a continuous manner, the second sampling is performed. In this case, detection of the liquid level in the sample vessel may be abbreviated.

⑩ In a similar manner, the sample 15 is applied to the second test piece 18.

⑪ After applying the next sample, the hole closing action is performed as in step ⑧.

⑫ After application of the second sample to the last test piece is completed (in the example), the sample rack 13 returns to the fixed position of the sample vessel 14, and the nozzle 11 reverts to a tip discarding action. The discarding action is performed by hanging the pipette tip 32 on a tip removing device 34 that is cut in a U-shape, and then by elevating the nozzle assembly 6. Then, the nozzle assembly 6 returns to the first ready or standby position.

⑬ On the other hand, during the time from fitting of the tip to the time of applying a sample to the first test piece, the test piece table 2 moves so that the black damping cones 24 and the standard reflex piece 23 are positioned in turn under the photometric assembly 4. After the photometric measurements are made, a correction or calibration of reflectivity is performed. Hereafter, the table 2 stops at a position wherein the reagent layer of the test piece 18 comes under each applying hole 8 of the sample liquid applying part 3.

⑭ After finishing all sample applying processes, the test piece table 2 is advanced slightly (Y direction) and after a specified time, the reflectivity of each reagent layer is measured at the photometric assembly 4. The data which are obtained are stored by the microcomputer, converted to a concentration of the measured substance, or to another measurement value based on the calibration data stored in advance. After measurement is finished, the test piece is removed and, if necessary, another test piece is set in place, and the above steps ①- ⑭ are repeated.

Figure 2:
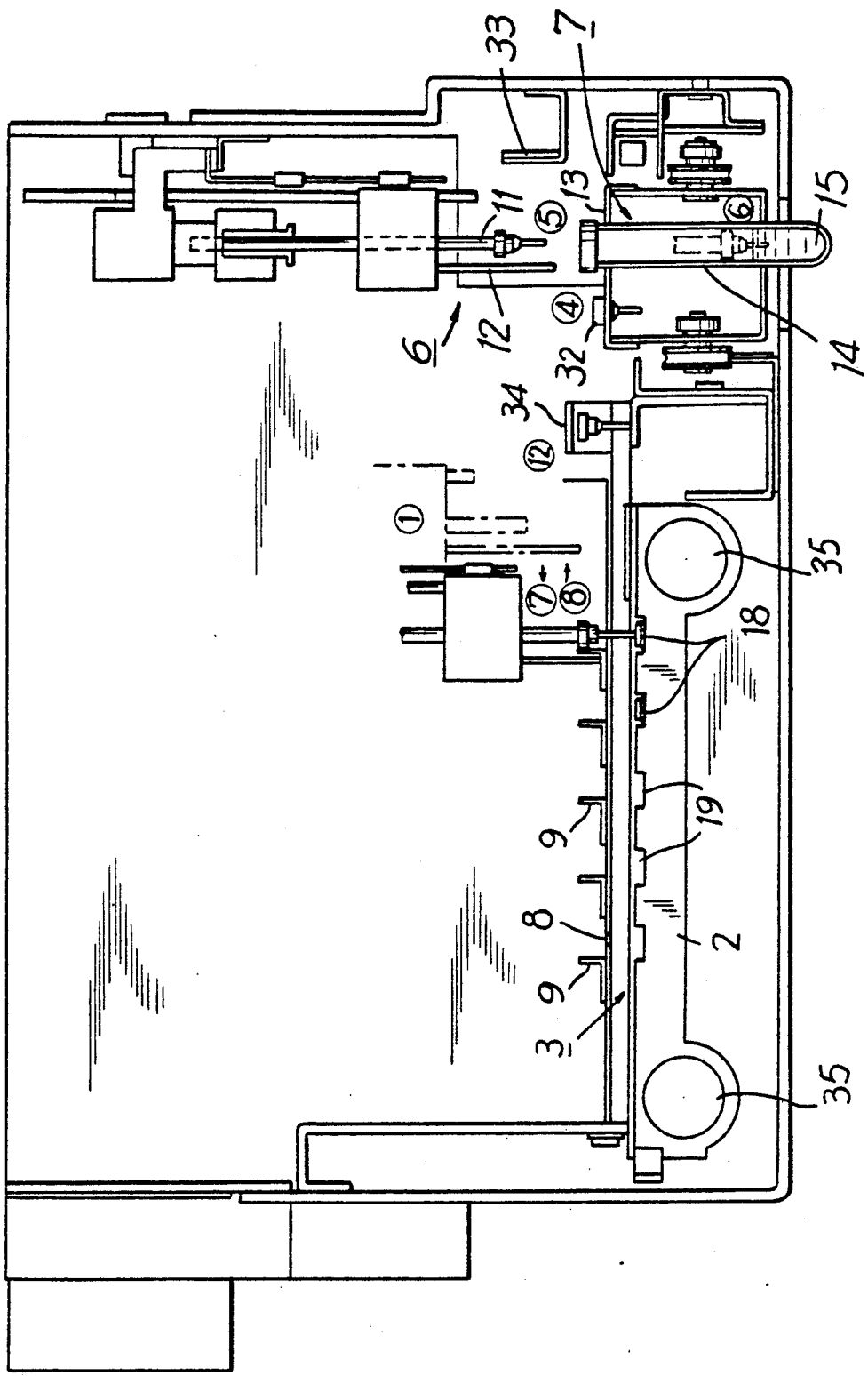
FIG. 2 is a front view thereof including a nozzle assembly.

In FIG. 2, rods 35 guide the test piece table 2 in their motion in the Y direction. The table 2 is driven by a pulse motor (not shown), that is controlled by the microcomputer. Similarly, the nozzle assembly 6 is driven by two pulse motors (not shown), separately. The nozzle 11 and the cover opening-closing rod 12 may be separately driven.

An example wherein a slide-shutter is used as the cover in an alternative embodiment in accordance with the invention, will be described in the following.

Figure 5:
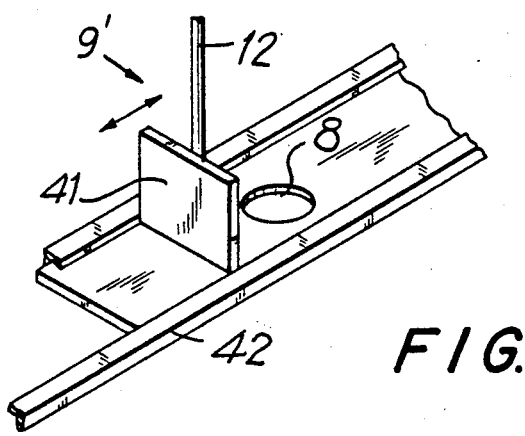
FIG. 5 is a perspective view showing an alternative embodiment of a cover in accordance with the invention.

FIG. 5 is a perspective view showing only a segment of the apparatus near a cover 9 and the associated applying hole 8. A moving right-angle element 41 is located at the hole, and is moved by pushing with a cover opening-closing rod 12. The cover 9' moves along the edge guide 42. In place of the edge guide 42, a groove may be used in another alternative embodiment. Further, the opening and closing of the cover may be automatically performed by the use of a spring.

The case wherein two single item test pieces 18 were used, was described above. Operation on a multi-item test piece 16 is similarly performed. In this situation, several items can be measured by setting only one test piece 16 in the groove 17 of the apparatus. This type of measurement is extremely convenient and accurate.

As described above in detail, in the invention, a plurality of applying holes are arranged in a row with specified spacing therebetween in a sample liquid applying part or station. The sample liquid applying station is arranged at the upper part of a movable test piece table, and a cover is provided adjacent each applying hole. The cover includes a cover piece and a moving piece that intersect to form an L-shape, and there is a supporting shaft along the intersection that allows pivoting of the cover. A cover opening-closing rod opens or closes the cover by pushing the cover piece and moving piece, respectively, in synchronism with the nozzle used for applying a sample to the test piece.

Accordingly, in the case of concurrent multi-measurements such as the set test or profile test of blood samples, water evaporation from a sample, after applying the sample to a reagent, can be prevented by use of covers, and temperature is maintained more uniformly, assuring accurate analysis. Further, the structure of the apparatus is simple, and it is low in cost to produce because opening or closing the covers is performed by making use of the action of the sampling nozzle, rather than by a separate mechanism. This is a very advantageous construction.

I claim:

1. A method for chemically analyzing a sample using an apparatus including a test piece table, a sample applying station having a plurality of applying holes arranged at specified intervals, a reagent layer constant temperature chamber, a measuring station, said sample applying station having a sample applying nozzle, movable hole covers, and a rod for opening and closing said covers, comprising the steps:

positioning a test piece on said test piece table, said test piece including a plurality of reagent layers;

moving said test piece table to locate each said reagent layer beneath a respective one of said applying holes;

applying from above a portion of said sample to each said reagent layer in sequence, said sample portion being applied through the associated applying hole by said applying nozzle;

covering each said hole with a respective one of said covers in sequence after said sample portion is applied, each said cover having a cover piece and a moving piece joined at a connection into an L-shaped, a cover supporting shaft being fitted along said connection, said step of covering comprising moving said rod for opening and closing to pivot said covers about said shaft in sequence with application of said sample portions, said step of applying sample portions being effected by moving said sample applying nozzle over each said applying hole in sequence;

moving said testpiece table to said measuring station; and measuring said sample on said test piece.

2. A method for chemically analyzing a sample using an apparatus including a test piece table, a sample applying station having a plurality of applying holes arranged at specified intervals, a reagent layer constant temperature chamber, a measuring station, said sample applying station having a sample applying nozzle, movable hole covers, and a rod for opening and closing said covers, comprising the steps:

positioning a test piece on said test piece table, said test piece including a plurality of reagent layers;

moving said test piece table to locate each said reagent layer beneath a respective one of said applying holes;

applying from above a portion of said sample to each said reagent layer in sequence, said sample portion being applied through the associated applying hole by said applying nozzle;

covering each said hole with a respective one of said covers in sequence after said sample portion is applied, wherein the cover includes a slide-shutter having a moving part projecting upward, and the rod for opening and closing said covers, which operates by pushing the moving part, is moved in synchronism with the sample applying nozzle;

moving said test piece table to said measuring station; and measuring said sample on said test piece.

3. A method for chemically analyzing a sample using an apparatus including a test piece table, a sample applying station having a plurality of applying holes arranged sideways at specified intervals, a reagent layer constant temperature chamber, a measuring station, said sample applying station having a sample applying nozzle, movable hole covers, and a rod for opening and closing said covers, comprising the steps;

positioning a test piece on said test piece table, said test piece including a plurality of reagent layers;

moving said test piece table to locate each said reagent layer beneath a respective one of said applying holes;

applying from above a portion of said sample to each said reagent layer in sequence, said sample portion being applied through the associated applying hole by said applying nozzle;

covering each said hole with a respective one of said covers in sequence after said sample portion is applied, each said cover having a cover piece and a moving piece connected into an L-shape, a cover supporting shaft being fitted at said connection, said step of covering comprising moving said rod for opening and closing to push said covers in synchronism with application of said sample portions by said sample applying nozzle;

moving said test piece table to said measuring station; and measuring said sample on said test piece.

4. A method for chemically analyzing a sample using an apparatus including a test piece table, a sample applying station having a plurality of applying holes arranged sideways at specified intervals, a reagent layer constant temperature chamber, a measuring station, said sample applying station having a sample applying nozzle, movable hole covers, and a rod for opening and closing said covers, comprising the steps:

positioning a said test piece on test piece table, said test piece including a plurality of reagent layers;

moving said test piece table to locate each said reagent layer beneath a respective one of said applying holes;

applying from above a portion of said sample to each said reagent layer in sequence, said sample portion being applied through the associated applying hole by said applying nozzle;

covering each said hole with a respective one of said covers in sequence after said sample portion is applied, wherein the cover includes a slide-shutter having a moving part projected upward, and the rod for opening and closing said covers, which operates by pushing the moving part, is moved in synchronism with the sample applying nozzle, said step of applying sample portions being effected by moving said sample applying nozzle over each said hole in sequence;

moving said test piece table to said measuring table; and measuring said sample on said test piece.

5. A method for chemically analyzing a sample using an apparatus including a test piece table, a sample applying station having a plurality of applying holes arranged sideways at specified intervals, a reagent layer constant temperature chamber, a measuring station, said sample applying station having a sample applying nozzle, movable hole covers, and a rod for opening and closing said covers, comprising the steps:

positioning a test piece on said test piece table, said test piece including a plurality of reagent layers;

moving said test piece table to locate each said reagent layer beneath a respective one of said applying holes;

applying from above a portion of said sample to each said reagent layer in sequence, said sample portion being applied through the associated applying hole by said applying nozzle, said applying being done in sequence beginning with the reagent layer requiring the longer time after applying before measurement is started;

covering each said hole with a respective one of said covers in sequence after said sample portion is applied, each said cover having a cover piece and a moving piece connected at a joint into an L-shape, a cover supporting shaft being fitted at said joint, said step of covering comprising moving said rod for opening and closing to push said covers in synchronism with application of said sample portions, said step of applying sample portions being effected by moving said sample applying nozzle over each said hole in sequence;

moving said test piece table to said measuring station; and measuring said sample on said test piece.

6. A method for chemically analyzing a sample using an apparatus including a test piece table, a sample applying station having a plurality of applying holes arranged sideways at specified intervals, a reagent layer constant temperature chamber, a measuring station, said sample applying station having a sample applying nozzle, movable hole covers, and a rod for opening and closing said covers, comprising the steps:

positioning a test piece on said test piece table, said test piece including a plurality of reagent layers;

moving said test piece table to locate each said reagent layer beneath a respective one of said applying holes;

applying from above a portion of said sample to each said reagent layer in sequence, said sample portion being applied through the associated applying hole by said applying nozzle, said applying being done in sequence beginning with the reagent layer requiring the longer time after applying before measurement is started;

covering each said hole with a respective one of said covers in sequence after said sample portion is applied, wherein said cover includes a slide-shutter having a moving part projecting upward and said rod for opening and closing, which operates by pushing the moving part, is moved in synchronism with said sample applying nozzle;

moving said test piece table to said measuring station; and measuring said sample on said test piece.

7. An apparatus for chemically analyzing a sample contained on a test piece including a reagent layer, said apparatus comprising:
- a test piece table means for setting the test piece thereon;
- an applying station means positioned and arranged such that a sample may be applied to the reagent layer;
- said applying station means including a plurality of holes and covers positioned and arranged to open and shut said holes freely, one of said covers positioned on each of said applying holes, each of said covers including a cover piece and a moving piece connected at a joint into a L-shape, a supporting shaft positioned and arranged along said joint;
- a rod positioned and arranged for opening and closing said covers;
- and a sample applying nozzle positioned and arranged for depositing samples onto the test piece through said applying holes, said rod and nozzle constructed so as to be moving in synchronism, said rod constructed and arranged so that its movement will open and close the associated covers by pushing said cover piece and moving said cover piece to pivot about said shaft;
- a measuring station means for measuring the reaction between the sample and the reagent layer, said measuring station means being elevated above said table means;
- and said test piece table means being constructed and arranged so that its movement will selectably position the test piece at the applying station means and the measurement station means.

8. An apparatus for chemically analyzing a sample contained on a test piece including a reagent layer, said apparatus comprising:
- a test piece table means for setting the test piece thereon;
- an applying station means positioned and arranged such that a sample may be applied to the reagent layer;
- a measuring station means for measuring the reagent between the sample and the reagent layer, said measuring station means being elevated above said table means;
- a sample applying nozzle positioned and arranged for depositing samples onto the test piece at said applying station means;
- said applying station means including a plurality of holes and covers positioned and arranged to open and shut said holes freely, one of said covers positioned on each of said applying holes,
- a rod positioned and arranged for opening and closing said covers;
- each of said covers including a slide shutter having a moving part projecting upwardly, and said rod being arranged so as to be in synchronism with said sample applying nozzle so as to operate said covers by pushing said moving part;
- said test piece table means being constructed and arranged so that its movement will selectably position the test piece at the applying station means and the measurement station means.

* * * * *